United States Patent
Aki et al.

(10) Patent No.: US 9,440,912 B2
(45) Date of Patent: Sep. 13, 2016

(54) PENTENENITRILE ISOMERIZATION

(71) Applicant: INVISTA NORTH AMERICA S.A R.L., Wilmington, DE (US)

(72) Inventors: Sudhir N. V. K. Aki, Katy, TX (US); William J. Tenn, III, Beaumont, TX (US); Thomas E. Vos, Beaumont, TX (US)

(73) Assignee: INVISTA NORTH AMERICA S.A.R.L., Wilmington, DE (US)

( * ) Notice: Subject to any disclaimer, the term of this patent is extended or adjusted under 35 U.S.C. 154(b) by 0 days.

(21) Appl. No.: 14/649,644

(22) PCT Filed: Dec. 5, 2013

(86) PCT No.: PCT/US2013/073396
§ 371 (c)(1),
(2) Date: Jun. 4, 2015

(87) PCT Pub. No.: WO2014/089347
PCT Pub. Date: Jun. 12, 2014

(65) Prior Publication Data
US 2015/0299106 A1    Oct. 22, 2015

Related U.S. Application Data

(60) Provisional application No. 61/734,525, filed on Dec. 7, 2012.

(30) Foreign Application Priority Data

Mar. 15, 2013 (GB) .................................. 1304808.7

(51) Int. Cl.
| | | |
|---|---|---|
| C07C 235/30 | (2006.01) |
| C07C 255/07 | (2006.01) |
| B01J 23/06 | (2006.01) |
| B01J 23/10 | (2006.01) |
| B01J 23/26 | (2006.01) |
| B01J 23/70 | (2006.01) |
| C07C 253/30 | (2006.01) |
| B01J 21/08 | (2006.01) |
| B01J 21/10 | (2006.01) |
| B01J 23/20 | (2006.01) |
| B01J 23/30 | (2006.01) |
| B01J 23/44 | (2006.01) |
| B01J 27/053 | (2006.01) |
| B01J 29/18 | (2006.01) |

(52) U.S. Cl.
CPC .............. *C07C 253/30* (2013.01); *B01J 21/08* (2013.01); *B01J 21/10* (2013.01); *B01J 23/06* (2013.01); *B01J 23/10* (2013.01); *B01J 23/20* (2013.01); *B01J 23/26* (2013.01); *B01J 23/30* (2013.01); *B01J 23/44* (2013.01); *B01J 27/053* (2013.01); *B01J 29/18* (2013.01)

(58) Field of Classification Search
CPC .... C07C 253/30; C07C 255/07; B01J 23/06; B01J 23/10; B01J 23/26; B01J 21/066; B01J 23/70
See application file for complete search history.

(56) References Cited

U.S. PATENT DOCUMENTS

| | | | |
|---|---|---|---|
| 3,526,654 A | 9/1970 | Hildebrand | |
| 7,612,224 B2 * | 11/2009 | Scheidel | ............... C07C 253/30 558/355 |
| 2006/0194979 A1 | 8/2006 | Bartsch et al. | |
| 2007/0287851 A1 | 12/2007 | Scheidel et al. | |

OTHER PUBLICATIONS

Duffy, J. A.,"Ionic-Covalent Character of Metal and Nonmetal Oxides",J. Phys. Chem. A, vol. 110, 2006, pp. 13245-13248.
International Search Report Received for PCT Application No. PCT/US2013/073396, mailed on Mar. 5, 2014, 3 pages.
International Preliminary Report on Patentability and Written Opinion Received for PCT Application No. PCT/US2013/073396, issued on Mar. 18, 2015, 11 pages.

* cited by examiner

*Primary Examiner* — Valerie Rodriguez-Garcia
(74) *Attorney, Agent, or Firm* — Robert B. Furr, Jr.; Edward F. Kenehan, Jr.

(57) ABSTRACT

Disclosed is a process for isomerizing cis-2-pentenenitrile to 3-pentenenitrile in the presence of a non-aluminum metal oxide catalyst, wherein: (a) the metal in the catalyst has an oxidation state in the range from +1 to +4; (b) the metal has a cation radius in the range from 0.35 to 1.0 Å; (c) the metal of the catalyst has a polarizing power, C/r, is in the range from 2 to >8, wherein C is the charge of the metal and r is the ionic radius in Å; (d) the bond network of the catalyst has a % ionicity of >20; (e) the metal oxide has an acidity strength in the range from strong to very weak; and (f) the metal oxide has a basicity (nucleophilicity) strength of weak to strong.

8 Claims, No Drawings

PENTENENITRILE ISOMERIZATION

CROSS-REFERENCE TO RELATED APPLICATIONS

This application claims benefit of the filing date of U.S. Provisional Patent Application No. 61/734,525, filed Dec. 7, 2012 and Great Britain Patent Application No. 1304808.7 filed on Mar. 15, 2013, the contents of which are all specifically incorporated herein by reference in their entireties.

The present invention relates to a process for isomerizing cis-2-pentenenitrile to 3-pentenenitrile and, in particular, to the use of metal oxides to catalyze such a reaction.

BACKGROUND OF THE INVENTION

Commercial processes for producing adiponitrile, an important intermediate in the manufacture of nylon-6,6 and related products, typically include a stage in which 3-pentenenitrile (or 4-pentenenitrile) is hydrocyanated in the presence of a nickel (0) catalyst to form adiponitrile. It is known that cis-2-pentenenitrile is formed as a byproduct during such a hydrocyanation. The formation of cis-2-pentenenitrile represents an adiponitrile yield loss in the process. Furthermore, the accumulation of cis-2-pentenenitrile during the hydrocyanation reaction is undesirable because it behaves as a catalyst poison. However, the removal of cis-2-pentenenitrile is not straightforward. It can be separated from unreacted 3-pentenenitrile by distillation. Alternatively, it can be removed by reaction with an alkali metal sulfite and bisulfite solution but this can complicate the procedure. With this in mind, rather than physically removing the cis-2-pentenenitrile, efforts have focused on converting it to a useful product. In this regard, it is preferred to isomerize cis-2-pentenenitrile to 3-pentenenitrile, which can then be recycled back into the hydrocyanation reaction.

The isomerization of cis-2-pentenenitrile to 3-pentenenitrile has been described in U.S. Pat. No. 3,526,654 and U.S. Patent Publication No. 2006/0194979. Both describe that the isomerization reaction may be carried out in the presence of an aluminium oxide catalyst. In U.S. Pat. No. 3,526,654, the aluminium oxide catalyst used is Alcoa F-1, while in U.S. Patent Publication No. 2006/0194979, the aluminium oxide catalyst has a BET surface area of at least 50 m$^2$/g.

SUMMARY OF THE INVENTION

Against this background, the present inventors have identified that, from a performance point of view, it is desirable to identify non-aluminium metal oxide catalysts for catalysing the isomerization of cis-2-pentenenitrile to 3-pentenenitrile. However, the class of metal oxide catalysts is very broad and not all metal oxide catalysts are suitable to catalyze this particular isomerization reaction. In particular, some metal oxide catalysts simply do not work and there is no conversion from cis-2-pentenenitrile to 3-pentenenitrile. For other metal oxide catalysts, while they may be effective in catalysing conversion of cis-2-pentenenitrile to 3-pentenenitrile, there are associated drawbacks such as poor selectivity for 3-pentenenitrile and/or the production of unacceptably high levels of byproducts.

A particular problem in this regard is the accumulation of C10-dinitrile (DDNs) byproducts, which can be problematic even at low levels. In this regard, pentenenitrile oligomers behave as catalyst poisons as they accumulate and the samples become more viscous as the oligomerization reaction progresses, and the catalyst becomes coated in heavies. Furthermore, if the target adiponitrile product contains DDNs (which it will if the 3-pentenenitrile produced contains DDNs), some of the DDNs will form cyclic Schiff bases when the adiponitrile is subsequently hydrogenated to hexamethylenediamine. These cyclic Schiff bases behave as chain terminators during the subsequent synthesis of nylon-6,6, producing a lower quality nylon polymer.

Following an extensive investigation of the reactions which are taking place, the inventors have identified a subclass of metal oxide catalysts which are particularly effective at catalysing the isomerization of cis-2-pentenenitrile to 3-pentenenitrile, while avoiding the problematic buildup of DDN byproducts.

Therefore, the present invention provides a process for isomerizing cis-2-pentenenitrile to 3-pentenenitrile in the presence of a non-aluminium metal oxide catalyst, wherein:
(a) the metal in the catalyst has an oxidation state in the range from +1 to +4;
(b) the metal has a cation radius in the range from 0.35 to 1.0 Å;
(c) the metal of the catalyst has a polarising power, C/r, is in the range from 2 to >8, wherein C is the charge of the metal and r is the ionic radius in Å;
(d) the bond network of the catalyst has a % ionicity of >20;
(e) the metal oxide has an acidity strength in the range from strong to very weak; and
(f) the metal oxide has a basicity (nucleophilicity) strength of weak to strong.

Advantageously, where non-aluminium metal oxide catalysts which satisfy the requirements (a) to (f) are used to catalyze the isomerisation of cis-2-pentenenitrile to 3-pentenenitrile, good conversion, good selectivity and the production of minimal levels of unwanted byproducts are observed.

In this regard, the present inventors are the first to have identified the balance of properties which a non-aluminium metal oxide catalyst needs to have in order to be an effective and useful catalyst for the isomerization of cis-2-pentenenitrile to 3-pentenenitrile.

The isomerization process of the present invention is carried out by contacting the cis-2-pentenenitrile with the solid state non-aluminium metal oxide catalyst in either the liquid phase or the gas phase. In one embodiment, the process is carried out in the liquid phase. The process is carried out at a temperature in the range from 50 to 250° C., in one embodiment, at a temperature in the range from 125 to 200° C. The pressure at which the isomerization reaction is performed is not critical and pressures in the range from 0.5 to 50 atmospheres are acceptable.

The isomerization process may be carried out in any reactor which is capable of containing a liquid or gaseous medium. An example of suitable apparatus is an evaporator for feeding cis-2-pentenenitrile in the vapour phase to a column containing the catalyst. Preferably, the isomerization process is carried out in a reactor capable of containing a liquid feed and the catalyst is in the form of a packed bed.

The source of the cis-2-pentenenitrile used as the starting material in the process of the invention is not limited although it will typically have been obtained as a by-product during the hydrocyanation of 3-pentenenitrile and 4-pentenenitrile in the presence of a Ni(0) catalyst in the production of adiponitrile.

Without wishing to be bound by theory, the isomerization of cis-2-pentenenitrile to 3-pentenenitrile involves the movement of the C=C double bond from the 2-position to the 3-position within the molecule. For this to occur, a proton must be removed from the framework at position C4 of cis-2-pentenenitrile and transferred to position C2. For a catalyst to be useful in catalysing this reaction, it needs to have the ability to deprotonate the cis-2-pentenenitrile framework, stabilise the deprotonated intermediate compound and transfer the proton to the C2 position. This requires that the catalyst has a bifunctional ability. In this regard, it needs to include both a Brønsted basic site to abstract the proton and a Lewis acid site to adsorb the conjugated base of the proton i.e. the deprotonated intermediate, and the two sites need to be sufficiently close to each other that the transfer of the proton can occur. By careful study of a number of metal oxide catalysts, the inventors have identified that where the non-aluminium metal oxide catalyst satisfies features (a) to (f) above, these requirements are met.

Typically, binary metal oxides are essentially ionic network structures. The surfaces of such oxide materials involve defects where oxide species and metal centres remain exposed and coordinatively unsaturated at the surface. These sites would be associated with a very high free energy and so would be very unstable. Therefore, to stabilize the surface, reaction with molecules from the environment e.g. water and surface reconstruction occur which limits the number of coordinatively unsaturated centres. However, unsaturated centres at the surface can remain or be generated by desorption of water. Therefore, the surface of solid metal oxides can consist of surface coordinatively unsaturated cations which act as Lewis acid sites and surface oxide anions which can act as Brønsted basic sites.

The first condition which the non-aluminium metal oxide catalyst should meet is that it has an oxidation state in the range from +1 to +4 (feature (a)). The oxidation state of the metal has an important impact on the acido-basicity of the metal oxide catalyst in that it is a factor which contributes towards the polarising power of the metal and it influences the ionicity of the bond network of the catalyst, both of which determine the Lewis acidity/Brønsted basicity of the catalyst. In one embodiment, the metal has an oxidation state within the range from +2 to +4.

The metal has a cation (ionic) radius in the range from 0.35 to 1.0 Å. In one embodiment, the metal has a cation radius in the range from 0.5 to 0.9 Å. The radius of the metal cation (feature (b)) is important in determining the polarising power of the metal. In particular, the polarising power (feature (c)) of the metal is a measure of the ability of the metal to attract the shared pair of electrons towards itself. The polarising power is calculated as follows:

Polarizing power=$C/r$ wherein C is the charge of the metal ion and r is the radius of the metal cation in Å. The larger the metal cation and the lower its charge, the less Lewis acidic it will be and, in parallel, the stronger the basicity of the oxide anions. There are a number of different methods with which the skilled person will be familiar which may be used to determine the radius of a metal cation. An example of such a technique uses X-ray crystallography data.

In this regard, the metal of the catalyst used in the process of the invention has a polarising power, C/r, in the range from 2 to >8, wherein C is the charge of the metal and r is the cation (ionic) radius in Å. In one embodiment, the metal has a polarising power in the range from 4 to 8. As described above, both Lewis acidic and Brønsted basic sites are required for pentenenitrile isomerisation to be catalyzed by a metal oxide. The larger a cation and the lower its charge, the less Lewis acidic it will be, and in parallel the stronger the basicity of the oxide anions. A balance between these two properties is reflected by the polarizing power of the metal oxide, with a range of 2 to >8 reflecting a metal oxide that has an appropriate degree of basicity and acidity to be useful.

The ionicity of the bond network of the metal oxide (feature (d)) will have an impact on the basicity of the oxide and hydroxide species which are at the surface of the metal oxide and which function to deprotonate the cis-2-pentenenitrile. In this regard, the bond network of the metal oxide has ionicity of 20% or greater, in one embodiment 30% or greater, in one embodiment, 40% or greater. By ensuring that the ionicity falls within this range, the metal oxide catalyst has the required balance of acidity and basicity so that it can effectively deprotonate the cis-2-pentenenitrile and also stabilise the deprotonated intermediate which is formed and facilitate transfer of the proton. The ionicity of the bond network of a metal oxide can be calculated by a number of techniques, for example using the technique set out in Duffy, J. Phys. Chem. A, 2006, 110, 13245-13248, the contents of which is incorporated by reference.

As described above, the non-aluminium metal oxide catalyst used in the process of the invention is bifunctional in that it has both Lewis acid sites and Brønsted basic sites. In this regard, the Brønsted basic sites have a basicity (also referred to a nucleophilicity) strength (feature (e)) in the range from weak to strong. This ensures that the surface of the metal oxide is sufficiently basic that it can deprotonate the cis-2-pentenenitrile. The Lewis acid sites have an acidity in the range from strong to very weak (feature (f)). This means that Lewis acid sites can stabilise the deprotonated intermediate which is formed during the isomerisation reaction. One factor which influences the acido-basicity characteristics of a metal oxide is the calcination temperature at which it is prepared.

Preferably, the non-aluminium metal oxide used as a catalyst in the process of the invention is selected from the group consisting of γ-$Al_2O_3$, β-$Ga_2O_3$, $Fe_2O_3$, $Cr_2O_3$, $La_2O_3$, $SnO_2$, $ZrO_2$, $CeO_2$, $ThO_2$, MgO, CoO, NiO, CuO, ZnO and mixtures thereof. These metal oxides satisfy the features (a) to (f) which are described above and so have been found to be particularly effective catalysts in that they are associated with good conversion of cis-2-pentenenitrile, good selectivity and the production of low levels of unwanted byproducts. In particular, $Cr_2O_3$, $La_2O_3$, $ZrO_2$ and ZnO are preferred.

The metal oxide catalysts used in the process of the invention are commercially available. Examples of suitable catalysts include but are not limited to X-410® Chromium oxide catalyst tablets available from Calsicat, ZN-0401® zinc oxide catalyst pellets from Engelhard, and MELCat XZO1526, XZO1580, and XZO1291® series of doped zirconium oxides available from MEL Chemicals.

Alternatively, suitable metal oxide catalysts may be prepared using techniques with which the person skilled in the art will be familiar.

As described above, by using the described non-aluminium metal oxide catalysts in the isomerization method of the present invention, several advantages are observed, specifically, good conversion of cis-2-pentenenitrile, an improvement in selectivity for 3-pentenenitrile and a reduction in the production of unwanted pentenenitrile byproducts.

During the isomerization of cis-2-pentenenitrile to 3-pentenenitrile, the selectivity for pentenenitrile isomerization is a linear function of conversion; the higher the conversion of cis-2-pentenenitrile, the lower the selectivity to 3-pentenenitriles. Hence, it is advantageous to achieve the appropriate balance between conversion and selectivity. In this regard, in one embodiment, the isomerization process of the present invention has a degree of conversion of cis-2-pentenenitrile to 3-pentenenitrile of about 10% or more, in one embodiment, about 20% or more, in one embodiment, about 30% or more, in one embodiment, about 40% or more, in one embodiment, about 50% or more.

In one embodiment, the isomerization process of the present invention has a degree of selectivity for 3-pentenenitrile of about 50% or more, in one embodiment, about 60% or more, in one embodiment, about 70% or more, in one embodiment, about 80% or more, in one embodiment, about 90% or more.

In an industrial adiponitrile plant, it is important that the adiponitrile produced has a low content of unwanted pentenenitrile oligomers such as DDN. From a commercial perspective, this limit is typically of the order of about 500 ppm by weight or less. There are several steps in which unwanted pentenenitrile oligomers, in particular DDNs, may be generated during the production of adiponitrile and the isomerization step with which the present invention is concerned is just one of these steps. Therefore, it is important that the levels of DDNs produced in the process of the present invention are as low as possible. In this regard, preferably the maximum level of DDN formation during the isomerization process of the present invention is less than about 300 ppm by weight, in one embodiment less than about 200 ppm for every 10 wt % of cis-2-pentenenitrile starting material which is converted to 3-pentenenitrile and trans-2-pentenenitrile products.

In particular, the inventors have determined that the ratio of C10-dinitriles (DDNs) formed (wt %)/total of 3-pentenenitriles and trans-2-pentenenitriles (PNs) formed (wt %) that is acceptable is about 350 or less, preferably about 300 or less, preferably about 250 or less, preferably about 200 or less, preferably about 150 or less, preferably about 100 or less. The amount of DDNs formed and the amount of PNs formed are measurements with which the skilled person will be familiar.

The invention will now be described further by reference to the following examples which are not intended to be limiting on the scope of the claim.

EXAMPLES

Catalyst Preparation

The zirconia catalysts used in examples 1 to 4 were received from Daiichi Kigenso Kagaku Kogyo Co., Ltd. The zirconia catalysts used in examples 5-16 were obtained from MEL Chemicals, Inc. Niobium pentoxide was obtained from Saint Gobain. Zinc oxide was a product of Engelhard. Chromium oxide was obtained from SigmaAldrich. Magnesium oxide was obtained from SigmaAldrich. Hydrogen mordenite was obtained from Strem Chemicals. Titania-supported palladium catalysts were products of Mallinckrodt Chemicals Inc., Calsicat Division.

Prior to evaluation all catalyst materials were calcined in a muffle furnace under a nitrogen atmosphere. The calcination temperature used for each catalyst material under evaluation are detailed in Table 1.

Example 1

The experiment was conducted in a 10 mL serum bottle, using a temperature-regulated aluminum heating block. Mixing was accomplished using a magnetic stir bar. The heating block was enclosed in a nitrogen purge box. Serum bottles were charged with $CaO/ZrO_2$ 0.5 g, and cis-2-pentenenitrile (4.5 grams) inside a glove-box and then transferred to the heating block at the beginning of the experiment. The temperature of the heating block was maintained at 100° C. Samples were then removed at the desired intervals for analysis by gas chromatography. The analytical results are presented in Table 1.

Example 2

Example 1 was repeated except that $CeO_2/ZrO_2$ (13±5% $CeO_2$) was used as the catalyst. The analytical results are presented in Table 1.

Example 3

Example 1 was repeated except that $CeO_2/ZrO_2$ (25±5% $CeO_2$) was used as the catalyst. The analytical results are presented in Table 1.

Example 4

Example 1 was repeated except that $CeO_2/ZrO_2$ (25±3% $CeO_2$) was used as the catalyst. The analytical results are presented in Table 1.

Example 5

Example 1 was repeated except that $SiO_2/ZrO_2$ (3.5% $SiO_2$) was used as the catalyst. The analytical results are presented in Table 1.

Example 6

Example 1 was repeated except that $SO_4/ZrO_2$ (7% $SO_4$) was used as the catalyst. The analytical results are presented in Table 1.

Example 7

Example 1 was repeated except that $WO_3/ZrO_2$ (15% $WO_3$) was used as the catalyst. The analytical results are presented in Table 1.

Example 8

Example 1 was repeated except that $La_2O_3/ZrO_2$ (10% $La_2O_3$) was used as the catalyst. The analytical results are presented in Table 1.

Example 9

Example 1 was repeated except that $CeO_2/ZrO_2$ (17% $CeO_2$) was used as the catalyst. The analytical results are presented in Table 1.

Example 10

Example 1 was repeated except that $CeO_2/La_2O_3/ZrO_2$ (17% $CeO_2$/5% $La_2O_3$) was used as the catalyst. The analytical results are presented in Table 1.

Example 11

Example 1 was repeated except that La$_2$O$_3$/ZrO$_2$ (10% La$_2$O$_3$) was used as the catalyst. The analytical results are presented in Table 1.

Example 12

Example 1 was repeated except that CeO$_2$/ZrO$_2$ (17% CeO$_2$) was used as the catalyst. The analytical results are presented in Table 1.

Example 13

Example 1 was repeated except that CeO$_2$/La$_2$O$_3$/ZrO$_2$ (17% CeO$_2$/5% La$_2$O$_3$) was used as the catalyst. The analytical results are presented in Table 1.

Example 14

Example 1 was repeated except that La$_2$O$_3$/ZrO$_2$ (10% La$_2$O$_3$) was used as the catalyst. The analytical results are presented in Table 1.

Example 15

Example 1 was repeated except that CeO$_2$/ZrO$_2$ (17% CeO$_2$) was used as the catalyst. See Table 1 for analytical results.

Example 16

Example 1 was repeated except that CeO$_2$/La$_2$O$_3$/ZrO$_2$ (17% CeO$_2$/5% La$_2$O$_3$) was used as the catalyst. The analytical results are presented in Table 1.

Example 17

Example 1 was repeated except that MgO was used as the catalyst. The analytical results are presented in Table 1.

Example 18

Example 1 was repeated except that ZnO was used as the catalyst. The analytical results are presented in Table 1.

Example 19

Example 1 was repeated except that Cr$_2$O$_3$ was used as the catalyst. The analytical results are presented in Table 1.

Example 20

Example 1 was repeated except that Nb$_2$O$_5$ was used as the catalyst. The analytical results are presented in Table 1.

Example 21

Example 1 was repeated except that H-Mordernite was used as the catalyst. The analytical results are presented in Table 1.

Example 22

Example 1 was repeated except that H-Mordenite was used as the catalyst. The analytical results are presented in Table 1.

Example 23

Example 1 was repeated except that Pd/TiO$_2$ (0.1 wt % Pd loading) was used as the catalyst. The analytical results are presented in Table 1.

Example 24

Example 1 was repeated except that Pd/TiO$_2$ (0.5 wt % Pd loading) was used as the catalyst. The analytical results are presented in Table 1.

Example 25

Example 1 was repeated except that no catalyst was used. The analytical results are included in Table 1.

TABLE 1

| Example | Catalyst | Dopant wt % | Conv (%) | 3PN Sel (%) | % PN balance | DDN % | Calcination Temp (° C.) |
| --- | --- | --- | --- | --- | --- | --- | --- |
| 1 | CaO/ZrO$_2$ | 2 ± 1 | 21.4 | 56.7 | 93 | 6.29 | 300 |
| 2 | CeO$_2$/ZrO$_2$ | 13 ± 5 | 8.5 | 63.7 | 98 | 0.23 | 300 |
| 3 | CeO$_2$/ZrO$_2$ | 25 ± 5 | 3.6 | 68.8 | 99 | 0.07 | 300 |
| 4 | CeO$_2$/ZrO$_2$ | 25 ± 3 | 7.3 | 69.4 | 98 | 1.36 | 300 |
| 5 | SiO$_2$/ZrO$_2$ | 3.5 | 0 | 0 | 100 | 0 | 300 |
| 6 | SO$_4$/ZrO$_2$ | 7 | 0 | 0 | 100 | 0 | 300 |
| 7 | WO$_3$/ZrO$_2$ | 15 | 0 | 0 | 100 | 0 | 300 |
| 8 | La$_2$O$_3$/ZrO$_2$ | 10 | 2.4 | 56.6 | 99 | 0 | 300 |
| 9 | CeO$_2$/ZrO$_2$ | 17 | 1.9 | 64.2 | 99 | 0 | 300 |
| 10 | CeO$_2$/La$_2$O$_3$/ZrO$_2$ | 17% Ce/5% La | 3.2 | 31.2 | 98 | 0 | 300 |
| 11 | La$_2$O$_3$/ZrO$_2$ | 10 | 20.7 | 61 | 98 | 0.7 | 500 |
| 12 | CeO$_2$/ZrO$_2$ | 17 | 10.5 | 73.6 | 99 | 0.2 | 500 |
| 13 | CeO$_2$/La$_2$O$_3$/ZrO$_2$ | 17% Ce/5% La | 11.8 | 69.2 | 99 | 0.3 | 500 |
| 14 | La$_2$O$_3$/ZrO$_2$ | 10 | 24.7 | 56 | 96 | 1.63 | 600 |
| 15 | CeO$_2$/ZrO$_2$ | 17 | 11.5 | 70.2 | 99 | 0.35 | 600 |
| 16 | CeO$_2$/La$_2$O$_3$/ZrO$_2$ | 17% Ce/5% La | 14.5 | 51.8 | 96 | 0.42 | 600 |
| 17 | MgO | — | 0 | 0 | 100 | 0 | 600 |
| 18 | ZnO | — | 36.9 | 47.4 | 99 | 0.33 | 400 |
| 19 | Cr$_2$O$_3$ | — | 12.3 | 66.7 | 99 | 0.02 | 600 |
| 20 | Nb$_2$O$_5$ | — | 0.4 | 40.7 | 100 | 0 | 300 |
| 21 | H-Mordenite | — | 0 | 0 | 100 | 0 | 600 |

TABLE 1-continued

| Example | Catalyst | Dopant wt % | Conv (%) | 3PN Sel (%) | % PN balance | DDN % | Calcination Temp (° C.) |
|---|---|---|---|---|---|---|---|
| 22 | H-Mordenite | — | 0 | 0 | 100 | 0 | 800 |
| 23 | Pd/TiO$_2$ | 0.1 | 0 | 0 | 100 | 0 | 400 |
| 24 | Pd/TiO2 | 0.5 | 0 | 0 | 100 | 0 | 400 |
| 25 | None | — | 0 | 0 | 100 | 0 | — |

Conv % = percent cis-2-pentenenitrile converted = (2PNinitial-2PNfinal/2PNinitial)
3PN Sel % = selectivity to 3-pentenenitriles = (trans and cis-3-pentenenitriles produced/2PN conv)
Conditions: 100° C., pure cis-2PN, 2 hours.

The data presented in Table 1 represent evaluations of a number of materials for the catalytic isomerization of cis-2-pentenenitrile to 3-pentenenitriles. Examples 5-7, and 21-24 show no cis-2-pentenenitrile conversion under the reaction conditions presented in Table 1 with, respectively, silica-doped zirconia, sulfated zirconia, tungstated zirconia, hydrogen mordenite, 0.1 wt % palladium on titania, and 0.5 wt % palladium on titania.

By way of contrast, examples 11-16, and 18-19 show conversions of cis-2-pentenenitriles to 3-pentenenitirles of 10% or more. Examples 8-16 show that conversion of cis-2-pentenenitrle to 3-pentenenitriles increases with increasing temperature of calcination of the catalyst, but that there are increasing levels of byproduct formation (DDNs). As can be seen in example 25, control experiments at the same conditions as those used in Table 1, but with no catalyst present, show no isomerization of cis-2-pentenenitirle to 3-pentenenitriles.

On the basis of these data, the inventors have determined that the properties of metal oxide catalysts useful for isomerization of cis-2-pentenenitriles include: low-medium metal oxidation state (+1-+4), small to large cation size (0.35-1.0 Å), polarizing power of 2 to >8 C/r, a bond network having a % ionicity of >30, a Lewis acid type of acidity, acidity strength of strong to very weak, and a basicity/nucleophilicity of weak to strong.

Examples of materials having these properties include, but are not limited to: γ-Al$_2$O$_3$, β-Ga$_2$O$_3$, Fe$_2$O$_3$, Cr$_2$O$_3$, La$_2$O$_3$, SnO$_2$, ZrO$_2$, CeO$_2$, ThO$_2$, MgO, CoO, NiO, CuO, and ZnO.

The invention claimed is:

1. A process for isomerizing cis-2-pentenenitrile to 3-pentenenitrile comprising contacting cis-2-pentenenitrile with a non-aluminium metal oxide catalyst under conversion conditions including a temperature of 50 to 250° C. and a pressure from 0.5 to 50 atmospheres, wherein the non-aluminium metal oxide catalyst is a metal oxide selected from the group consisting of:

(i) ZrO$_2$ doped with Ce$_2$O$_3$ or La$_2$O$_3$ or both Ce$_2$O$_3$ and La$_2$O$_3$; and
(ii) Cr$_2$O$_3$, ZnO, Fe$_2$O$_3$, CoO, NiO, CuO and mixtures thereof;

and wherein:

(a) the metal in the catalyst has an oxidation state in the range from +1 to +4;
(b) the metal has a cation radius in the range from 0.35 to 1.0 Å;
(c) the metal of the catalyst has a polarising power, C/r, in the range from 2 to →8, wherein C is the charge of the metal and r is the ionic radius in Å;
(d) the bond network of the catalyst has a % ionicity of >20;
(e) the metal oxide has an acidity strength in the range from strong to very weak; and
(f) the metal oxide has a basicity (nucleophilicity) strength of weak to strong.

2. A process according to claim 1, wherein the metal oxide is selected from the group consisting of Cr$_2$O$_3$, ZnO and mixtures thereof.

3. A process according to claim 1, wherein the isomerization is carried out in the liquid phase.

4. A process according to claim 1, wherein the isomerization is carried out in the gas phase.

5. A process according to claim 1, wherein the isomerization is carried out at a temperature in the range from 120° C. to 200° C.

6. A process according to claim 1, wherein the metal of the catalyst has a polarising power, C/r, in the range from 4 to 8.

7. A process according to claim 1, wherein the metal has a cation radius in the range from 0.5 to 0.9 Å.

8. A process according to claim 1, wherein the metal in the catalyst has an oxidation state in the range from +2 to +4.

* * * * *